United States Patent [19]

Daculsi et al.

[11] Patent Number: 5,717,006
[45] Date of Patent: Feb. 10, 1998

[54] COMPOSITION FOR BIOMATERIAL; PREPARATION PROCESS

[75] Inventors: Guy Daculsi, Vigneux De Bretagne; Pierre Weiss, Nantes; Joel Delecrin, Nantes; Gael Grimandi, Nantes; Norbert Passuti, St Sebastien Sur Loire; François Guerin, Chevreuse, all of France

[73] Assignee: Centre National de la Recherche Scientifique (C.N.R.S.), Paris, France

[21] Appl. No.: 535,273

[22] PCT Filed: Feb. 8, 1995

[86] PCT No.: PCT/FR95/00150

§ 371 Date: Oct. 10, 1995

§ 102(e) Date: Oct. 10, 1995

[87] PCT Pub. No.: WO95/21634

PCT Pub. Date: Aug. 17, 1995

[30] Foreign Application Priority Data

Feb. 8, 1994 [FR] France ................................. 94 01414

[51] Int. Cl.⁶ ........................................................ A61F 2/28
[52] U.S. Cl. ............................ 523/115; 424/426; 623/11
[58] Field of Search .............................. 424/423, 426; 523/115; 623/11

[56] References Cited

FOREIGN PATENT DOCUMENTS

| 0 115 549 | 8/1984 | European Pat. Off. . |
| 0 511 868 | 11/1992 | European Pat. Off. . |
| 3 011 006 | 1/1991 | Japan . |
| 2 248 232 | 4/1992 | United Kingdom . |
| WO86/01113 | 2/1986 | WIPO . |

OTHER PUBLICATIONS

G. Daculsi et al., "Scanning and Transmission Electron Microscopy, and Electron Probe Analysis of the Interface Between Implants and Host Bone", Scanning Microscopy, vol. 4, No. 2, 1990, pp. 309–314.

G. Daculsi et al., "Effect of the macroporosity for osseous substitution of calcium phosphate ceramics", Biomaterials, 1990, vol. 11, pp. 86–88.

N. Passuh et al., "Macroporous Calcium Phosphate Ceramic Performance in Human Spine Fusion", Clinical Orthopaedics and Related Research, Nov. 1989, No. 248, pp. 169–175.

G. Daculsi et al., "Macroporous calcium phosphate ceramic for long bone surgery in humans and dogs. Clinical and histological study", Journal of Biomedical Materials Research, vol. 24, 1990, pp. 379–396.

Primary Examiner—Carlos A. Azpuru
Attorney, Agent, or Firm—Young & Thompson

[57] ABSTRACT

Composition for biomaterial for resorption/substitution of support tissues, dental tissues, bone tissues and osteoarticular tissues, which is made up of 40 to 75% by weight of a mineral phase comprising either a mixture of β tricalcium phosphate (A) and hydroxyapatite (B), in a ratio A:B of between 20:80 and 70:30, or calcium titanium phosphate $(Ca(Ti)_4(PO_4)_6)$ (C), and 60 to 25% by weight of a liquid phase comprising an aqueous solution of a polymer derived from cellulose. The mineral phase is a powder with a particle size 80 to 200 μm in diameter. Preferably, the liquid phase is hydroxypropyl cellulose, and the concentration of the polymer in the liquid phase is from 0.5 to 4% by weight. The composition is prepared by mixing the mineral phase and the polymer of the liquid phase in an aqueous solution of defined viscosity, and sterilizing the liquid composition thus obtained.

8 Claims, No Drawings

COMPOSITION FOR BIOMATERIAL; PREPARATION PROCESS

This application is a 371 of PCT/FR95/00150 filed Feb. 8, 1995.

The invention relates to an injectable composition of a biomaterial for filling support tissues, dental tissues, bone tissues and osteoarticular tissues, which is intended to generate a resorption/substitution function.

Bone substitutes based on calcium phosphate particles and a biological adhesive are known from the prior art.

Thus, in Ann. Oto. Rhino. Laryngol. 101:1992, G. DACULSI et al. have described the efficacy of a microporous biphasic calcium phosphate composition for obliteration of the mastoid cavity.

The same authors have also reported the efficacy of a macroporous biphasic calcium phosphate composition for surgical repair of long bones (Journal of Biomedical Materials Research, Vol. 24, 379–396) and in vertebral arthrodesis (Clinical Orthopaedics and Related Research, 248, 1989, 169–175).

Moreover, JP 3 011 006 describes a cement for hard tissues which comprises a mineral phase made up of at least 60% alpha tricalcium phosphate and hydroxyapatite and/or a calcium monophosphate; and a liquid phase comprising carboxymethylcellulose.

However, on account of the excessive solubility of α tricalcium phosphate, such a composition has the disadvantage of not being sufficiently stable to permit a process of absorption/substitution of the hard tissue. In addition, such a composition is liable to generate harmful inflammatory processes. In addition, this mixture constitutes a calcium ionomer which is unsuitable for injection after a few minutes as a result of the mixture hardening from the moment it is made up. This combination has a two-fold instability, a volumetric contraction with release of water after several days, and especially a drop in the viscosity after sterilization of the mixture in an autoclave. It does not permit the formation of a "ready-to-use", sterile, injectable material.

The present invention has been set the object of providing a biomaterial composition which is charged in the mineral phase, is rehabitable and can be injected by the percutaneous route.

In particular, this biomaterial must have the following properties:

It must be sterilizable.

It must not be toxic in vivo.

It must have a strong mineral charge inducing a mineralization front.

The dispersion agent must only have the role of vector and must disappear over time without harmful inflammatory reaction.

Its rheology must be such that it permits injection.

It must be easy to use.

This object has been achieved by the present invention, the subject matter of which is a composition for biomaterial for resorption/substitution of support tissues, dental tissues, bone tissues and osteoarticular tissues, which is made up of:

40 to 75% by weight of a mineral phase comprising either a mixture of β tricalcium phosphate (A) and hydroxyapatite (B), in a ratio A:B of between 20:80 and 70:30, or calcium titanium phosphate $(Ca(Ti)_4(PO_4)_6)$ (C), and 60 to 25% by weight of a liquid phase comprising an aqueous solution of a polymer derived from cellulose.

The calcium titanium phosphate (CTP) of formula $Ca(Ti)_4(PO_4)_6$ is preferably of the Nasicon-like calci-metallo-phosphate type.

The mineral phase advantageously comprises 40% compound (A) and 60% hydroxyapatite (B).

It consists of a high-temperature sinter which is ground and sized to powder or granules whose particles have a diameter of 80 μm to 200 μm upon preparation of the composition. The choice of the particle diameter is guided by the resorption kinetics on the one hand, and by the rheology upon injection on the other hand. Particles with a diameter smaller than 80 μm have resorption kinetics which are too rapid, and those with a diameter greater than 200 μm pose problems in terms of rheology upon injection.

The viscoelastic polymer of the liquid phase is a nonionic polymer, in particular hydroxypropyl methylcellulose. A preferred hydroxypropyl methylcellulose has a molar substitution by methyl groups of 19 to 24% and by hydroxypropyl groups of 4 to 12%. It has a high degree of polymerization. The mean weight-average molecular weight is greater than 100,000 and is advantageously between 500,000 and 1,000,000.

The aqueous phase is determining as regards the rheological properties and consequently the viscoelasticity of the final composition which is intended to be injected.

To this end, the polymer concentration is advantageously between 0.5 and 4%, preferably 0.5 and 2%, by weight relative to the weight of the aqueous phase.

The composition according to the invention is obtained by mixing the constituents of the mineral phase and of the aqueous phase.

The granules or the powder of β tricalcium phosphate or CTP and hydroxyapatite constituting the mineral phase are obtained as described by DACULSI et al. (Rev. Chir. Orthop., 1989, 75(2): 65–71).

Sterilization by ethylene oxide is not possible for a "ready-to-use" material. The components of the mixture have in fact to be sterilized in their dry form, which requires a manipulation by the surgeon prior to the injection. This manipulation is difficult and is not reproducible.

According to the invention, sterilization of the composition is carried out by dissolving the polymer constituent of the aqueous phase in water to a viscosity which is determined as a function of the desired final viscosity. The solution obtained is then mixed with the mineral phase, and the resulting composition is introduced into container vials which are sealed and sterilized in an autoclave at 121° C. for 20 minutes.

The initial viscosity of the composition (polymer concentration) must be adapted so as to obtain the viscosity desired after sterilization, that is to say the polymer concentration such as is defined hereinabove.

The composition according to the invention can be used as a material for osseous filling of hard tissues in the body, the material being intended to generate a resorption/substitution function. It can be used in particular as a filling material associated with articular implants or prostheses or as a filling material for tumour resections.

The invention thus also relates to a process for treating the human or animal body, comprising the administration, by percutaneous injection, of a composition according to the invention at a site normally occupied by a support tissue, dental tissue, bone tissue or osteoarticular tissue, in order to generate a function of resorption/substitution of this tissue.

An example of application is the replacement of intervertebral discs.

The composition can be injected by the percutaneous route.

The injection can be performed with the aid of a system comprising a sterilizable syringe and connection pieces equipped with disposable plungers, for example the system marketed by HAWE NEOS DENTAL including a syringe sterilized in an autoclave (ref. No. 440, Seringue Hawe-Centrix C-R®, Mark III) and connection pieces (ref. No. 445).

The results obtained in animals with an example of a composition according to the invention will be given hereinafter.

EXAMPLE OF COMPOSITION

Granules made up of 40% by weight of β tricalcium phosphate and 60% hydroxyapatite, of which 95% had a particle diameter of between 80 and 200 μm, mixed with an aqueous solution containing 2% hydroxypropyl methylcellulose which has a molar substitution by methyl groups of 19 to 24% and by hydroxypropyl groups of 4 to 12%, as well as a high degree of polymerization, were mixed together in such a way as to obtain a composition comprising 57.5% by weight of β tricalcium phosphate and hydroxyapatite.

The composition thus prepared was sterilized in an autoclave.

In Vivo Study in Beagle Dogs

A. Experimental Procedure

The two successive access routes described by R. K. GURR and P. McAFEE ("Roentgenographic and biomechanical analysis of lumbar fusions: A canine model"; J. Orthop. Res., 1989, 7: 838–848) were repeated, but without performing an operation on the open spinal canal; in contrast, destabilization was performed at two levels at L3/L4 and L4/L5.

The resection was limited to the supraspinous and interspinous ligaments between L3 and L5. The facetectomy included the caudal articular processes (AP) of L3, the cranial and caudal AP of L4, and, finally, the cranial AP of L5.

At the level of the anterior column, a discal resection was performed at L3/L4 and at L4/L5 after sectioning the ALL and discal fenestration.

The dog was placed in the ventral decubitus position, with the 4 legs secured. The lumbar spinous processes (SP) of L2, L3, L4, L5 and L6 were located in relation to the 13th rib, and the skin and the thoracolumbar fascia along the median line of the spinous processes were incised.

The common muscular mass was removed subperiosteally on each side using a rugine, thus permitting dissection of the laminae as far as the articular processes.

Haemostasis was ensured by tamponing and coagulation if necessary. A check was then made to locate with certainty the L3, L4 and L5 levels, and dissection of the base of the transverse processes (TP) was continued there.

This permitted location of the pedicle target: it was situated outside the articular mass on a horizontal line passing through the lower half of the base of the TP, aiming being carried out at 45° from the outside inwards and from posterior to anterior, in a strictly frontal plane.

The anterior approach to the lumbar spine was performed in the same operating session, from the left side in order to minimize the vascular risks with the vena cava.

The animal was placed in decubitus on its right with a block at the level of the thoracolumbar hinge in order fully to expose the left subcostal angle.

A number of dissections carried out on the corpses of Beagle dogs confirmed that direct access under the 13th rib permitted fairly easy access to the discal levels L3/L4 and L4/L5.

The cutaneous incision was traced on a line parallel to the lower edge of the 13th rib, about 3 to 4 cm below the same.

It started a good hand's breadth from the posterior incision in order to avoid any risk of cutaneous necrosis, and extended over ten centimeters or so.

The oblique muscles were dissociated in the direction of their fibres; respecting the transverse muscle permitted retroperitoneal detachment without risk of pneumoperitoneum, since in the dog the peritoneum adheres strongly to the deep fascia of the transverse muscle and tears easily.

This same muscle was released at the level of its spinal attachments and exposed the psoas and quadrate muscles of the loin concealing the anterior face of the spine.

The access to the vertebral bodies is barred by the left-side lumbar arteries and veins which were ligated and sectioned, as well as a lumbar splanchnic nerve.

The anterior muscular plane was freed using an H-type electric bistoury, forming two pediculate muscle flaps, then the anterior face of the discs was exposed using a spatula and gouge forceps. The aorta and the peritoneum were reclined and protected by a flexible valve under the vertebral body.

After renewed targeting by light amplifier, discal excision was performed: in a first stage, a discal window was cut with the dagger bistoury, and the nucleus was gradually hollowed out through this opening using curettes of increasing size.

Ablation was continued as far as the vertebral plates which were opened up in order to get to the spongy tissue zone.

The empty discal space was filled at the two levels by means of the injection system described hereinabove. The muscle flap was repositioned on the anterior face of the spine at several points, and the wall was reclosed in three planes, without drainage.

The multiphase material was injected under pressure into the empty discal space at L3/L4 and L4/L5, following osteosynthesis.

The animals were sacrificed 6 months later by lethal injection of Nesdonal®.

B. Results

Out of a group of 8 dogs, there were two with immediate neurological complications in the nature of paraplegia caused by damage to the central motor neuron. The animals were sacrificed at D6.

The 6 other dogs did not present any problems: they were walking again after 24 hours, and at the end of the first post-operative week they were running and playing.

These 6 dogs were sacrificed 6 months after the injection.

Histology sections were prepared after two and a half months, and practically mature new bone tissue was observed: the interparticulate osseous bridges recreate an osseous framework of tight meshes, and the bone has the distinct appearance of a lamellar structure.

Practically all the initial biomaterial was replaced by this architecture, which fact indicates good cellular diffusion into the product without inflammatory reaction.

These good results were confirmed after 6 months, at which time the new bone tissue had continued to mature.

Complementary studies of biocompatibility (injections at subcutaneous sites and into muscle and cartilage) additionally revealed good tolerance and rapid degradation of the injected material.

In Vivo Study in New Zealand White Rabbits (Female)

A. Experimental Procedure

The animals used in the study were all mature and of similar weight (about 2.8 kg). The injection site used was the intramedullary site of the femur.

Each animal was operated on in both femurs, but at different dates (minimum interval of one week between each operation), since the rabbit tolerates poorly the loss of blood occasioned by a bilateral operation. The left femur was always operated on first.

The limb being operated on was shaved a few minutes before the operation in a closed area separate from the operating room. No prophylaxis with antibiotics was used.

The anaesthesia protocol was as follows:
- 15 minutes before the operation, intramuscular injection of 250 mg of ketamine hydrochloride (Kétalar®, Parke Davis, Courbevoie);
- 1 to 2 minutes before the operation, local and intra-articular anaesthesia of the knee using a mixture of 1% lidocaine hydrochloride (Xylocaïne 1%®, Astra France, Nanterre) and 1% lidocaine hydrochloride+epinephrine at 1:100,000 (Xylocaïne adrénaline®, Astra France, Nanterre) in respective proportions of 2:3–1:3;
- peroperative compensation of blood losses by ml of Ringer Lactate and Glucose 5%® (Labo. Aguettant, Lyons), injected 3 times by an intravenous auricular route.

The operation was performed under strictly aseptic conditions.

The anaesthetized animal is placed in the dorsal decubitus position, with the 4 limbs secured. A block is slid under the knee, on the side being operated on, in order to maintain an approximately 30° flexion of this knee. The operation site is then disinfected using a polyvidone-iodine solution before and after the local and intra-articular anaesthesia.

The operation site is then isolated using a sterile drape which has an opening.

The steps are as follows:
- internal para-patellar cutaneous incision approximately 3 cm in length;
- coagulation, by forceps, of a stable vascular pedicle situated at the upper part of the incision;
- incision of the internal patellar wing and of the articular capsule;
- lateral luxation of the patella;
- drilling a channel in the trochlear groove using a bore bit of 2 mm diameter, the drilling being "guided" by the intramedullary anatomy of the femur;
- careful reaming of the intramedullary cavity with the aid of a bore bit of 4 mm diameter, the reaming being guided by the preceding drilling;
- copious washing of the medullary cavity of the femur with physiological saline in order to remove all the intramedullary fat and the bone debris from reaming;
- slow injection of the material (described hereinabove), in retrograde fashion, into the reamed medullary cavity of the femur;
- manual introduction of the implant (pin made of titanium alloy ($Ti_6Al_4V$) with a smooth surface 2.5 cm in diameter) in its entirety so that it does not protrude from the joint;
- cleaning with physiological saline and a spatula the surplus material evacuated upon introduction of the implant;
- repositioning of the patella;
- closure, in one plane, of the capsule and the patellar wing by an impermeable overcasting of Vicryl® Déc. 2;
- cutaneous closure by an impermeable overcasting of Vicryl® Déc. 2;
- cutaneous spraying, over the access route, of a film containing aureomycin.

Duration of the operation: about 25 minutes.

No antibiotic therapy was used during or after the operation.

All the animals were sacrificed by a lethal intravenous injection of 0.25 g of thiopental sodium (Nesdonal®, Spécia Rhône-Poulenc, Paris).

B. Results

1. Histological Analysis (12 Rabbits)

Histological sections prepared at 1, 3, 6 and 9 weeks revealed a centripetal progression of bone apposition with progressive colonization of the particles of the mineral phase, then appearance of lamellar bone, at the same time as the particles constituting the mineral phase disappear, particularly rapid at the epiphyseal site.

At 12 weeks, the particles of the epiphyseal site and of the metaphyseal and diaphyseal sites were fragmented in a substantial proportion and were colonized by a tight-mesh lamellar bone structure, organized to a large extent in the haversian mode.

The bone apposition on contact with the implant was $43.7 \pm 5.2$. The surface occupied by the particles of the mineral phase was $28.6 \pm 13.2\%$. No fibrous tissue was observed.

A comparative study with polymethyl methacrylate instead of the composition according to the invention revealed the appearance of a fibrillar network progressively colonized by a non-mineralized osteoid substance.

2. Mechanical Extraction Tests

The object of these tests was to evaluate the force needed to tear out the implants from the femoral shaft, at different time intervals.

The frozen femurs were cut on an Isomet Plus Precision Saw® machine, transversely, just above the upper end of the pin.

The anchoring system is made up of:
- an aluminium cup in which the distal epiphysis of the femur is fixed with the aid of a metered quantity of acrylic cement. By means of a self-centring device which fits on the cup and on the outer part of the implant, the femur is fixed in such a way that the implant is parallel to the axis of traction;
- a cardan shaft screwed to the centre of the lower part of the cup and providing for possible orientation in the three spatial planes.

The assembly consisting of cup and cardan shaft was joined to the surface plate of an MTS 810® machine (Material Testing System, U.S.A).

The traction system is made up of:
- a Black and Decker® mandrel with rack which holds the proximal end of the pin;
- a cable connecting the mandrel to the strain gauge, the latter being fixed on the movable part of the MTS 810® machine.

Practical Implementation

The speed of displacement of the traction cell was fixed at 0.5 mm per minute.

The tests were recorded on a plotting table. A typical force (Newton)/displacement (mm) curve was obtained for each sample.

The maximum resistance to extraction (Re in MPa) was determined using the formula: $Re = F/\pi DL$, F being the maximum force applied to the implant during the extraction test (in Newtons), D being the diameter of the implant (2.5 mm), L being the length of the implant in contact with the bone (30 mm).

The statistical analysis of the results was carried out in accordance with the ANOVA variance analysis test with a risk $\alpha = 0.05$.

The tests were carried out on 36 femurs. At 12 weeks, the resistance to extraction is on average 58.83 (±17.83) MPa for the composition according to the invention.

By comparison, in the case of the cement based on methyl methacrylate, the average resistance was 140.33 (±8.96) MPa.

We claim:

1. Composition for biomaterial for resorption/substitution of support tissues, dental tissues, bone tissues and osteoarticular tissues, which is made up of:

40 to 75% by weight of a mineral phase consisting essentially either of a mixture of β tricalcium phosphate (A) and hydroxyapatite (B), in a ratio A:B of between 20:80 and 70:30, or of calcium titanium phosphate $Ca(Ti)_4(PO_4)_6$ (C), and 60 to 25% by weight of a liquid phase comprising an aqueous solution of a nonionic polymer derived from cellulose.

2. Composition according to claim 1, wherein the mineral phase consists essentially of 40% compound (A) and 60% hydroxyapatite (B).

3. Composition according to claim 1, wherein the mineral phase is made up of a powder with a particle size of from 80 to 200 μm in diameter.

4. Composition according to claim 1, wherein the liquid phase comprises hydroxypropyl methylcellulose.

5. Composition according to claim 1, wherein the concentration of the polymer in the liquid phase is from 0.5 to 4% by weight.

6. Composition according to claim 1, wherein the concentration of the polymer in the liquid phase is from 0.5 to 2% by weight.

7. Composition according to claim 1, wherein the mineral phase consists essentially of 40 to 75% by weight of calcium titanium phosphate $Ca(Ti)_4(PO_4)_6$ (C).

8. Process for the preparation of a composition according to claim 1, comprising the steps of:

preparing an aqueous solution of the polymer by adjusting its viscosity as a function of the desired viscosity of the final composition;

mixing the prepared aqueous solution of the polymer with the mineral phase; and sterilizing the thus-obtained liquid composition.

* * * * *